United States Patent
Lee

(10) Patent No.: US 10,231,705 B2
(45) Date of Patent: Mar. 19, 2019

(54) ULTRASOUND DIAGNOSTIC APPARATUS AND OPERATING METHOD THEREOF

(71) Applicant: SAMSUNG MEDISON CO., LTD., Gangwon-Do (KR)

(72) Inventor: Jin-yong Lee, Gangwon-do (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 946 days.

(21) Appl. No.: 14/567,755

(22) Filed: Dec. 11, 2014

(65) Prior Publication Data
US 2015/0209011 A1 Jul. 30, 2015

(30) Foreign Application Priority Data
Jan. 28, 2014 (KR) .................. 10-2014-0010885

(51) Int. Cl.
*A61B 8/00* (2006.01)
*G06T 7/00* (2017.01)
(Continued)

(52) U.S. Cl.
CPC .............. *A61B 8/463* (2013.01); *A61B 8/06* (2013.01); *A61B 8/469* (2013.01); *A61B 8/481* (2013.01); *A61B 8/488* (2013.01); *A61B 8/5207* (2013.01); *A61B 8/5223* (2013.01); *A61B 8/565* (2013.01); *G01S 7/52063* (2013.01);
(Continued)

(58) Field of Classification Search
CPC .... A61B 8/00; A61B 8/02; A61B 8/06; A61B 8/065; A61B 8/0883; A61B 8/0891; A61B 8/14; A61B 8/461–8/465; A61B 8/469; A61B 8/488; A61B 8/5223; A61B 8/5246; A61B 8/5207; G06T 7/0012; G06F 3/048; G01S 7/52071; G01S 7/52073; G01S 7/52084; G01S 7/52085; G01S 7/527;
(Continued)

(56) References Cited

U.S. PATENT DOCUMENTS 4,982,343 A * 1/1991 Hourvitz ................ G09G 5/393
345/592
5,355,887 A 10/1994 Iizuka et al.
(Continued)

FOREIGN PATENT DOCUMENTS

WO 01/47421 A1 7/2001

OTHER PUBLICATIONS

Markl, Michael, Philip J. Kilner, and Tino Ebbers. "Comprehensive 4D velocity mapping of the heart and great vessels by cardiovascular magnetic resonance." Journal of Cardiovascular Magnetic Resonance 13.1 (2011): 7.*

*Primary Examiner* — Carolyn Pehlke
(74) *Attorney, Agent, or Firm* — McDermott Will & Emery LLP

(57) ABSTRACT

Disclosed are an ultrasound diagnostic apparatus and an operating method thereof. The operating method includes displaying an ultrasound image of a target object, receiving an ultrasound signal obtained from a moving object of interest (OOI) included in the target object, setting a first reference region in the ultrasound image, acquiring first moving path information of the OOI passing through the first reference region, based on the received ultrasound signal, and displaying the first moving path in the ultrasound image, based on the first moving path information.

15 Claims, 8 Drawing Sheets

(a)

821 (b) 822

(51) Int. Cl.
*G01S 7/52* (2006.01)
*G01S 15/89* (2006.01)
*A61B 8/08* (2006.01)
*A61B 8/06* (2006.01)

(52) U.S. Cl.
CPC ...... *G01S 7/52071* (2013.01); *G01S 7/52073* (2013.01); *G01S 7/52084* (2013.01); *G01S 15/8984* (2013.01); *G01S 15/8993* (2013.01); *G06T 7/0012* (2013.01); *A61B 8/0883* (2013.01); *A61B 8/461* (2013.01); *A61B 8/587* (2013.01); *G01S 15/8979* (2013.01); *G01S 15/8988* (2013.01)

(58) Field of Classification Search
CPC ............... G01S 7/5273; G01S 15/8979; G01S 15/8981; G01S 15/8984; G01S 15/8988
USPC .......................................... 345/418, 629, 639
See application file for complete search history.

(56) References Cited

U.S. PATENT DOCUMENTS

| | | | |
|---|---|---|---|
| 5,820,561 A | 10/1998 | Olstad et al. | |
| 5,947,903 A * | 9/1999 | Ohtsuki | A61B 8/06 600/455 |
| 6,211,888 B1 * | 4/2001 | Ohtsuki | G01S 7/52068 345/419 |
| 2010/0305440 A1 * | 12/2010 | Lee | G06T 7/20 600/441 |
| 2011/0208056 A1 * | 8/2011 | Datta | A61B 8/06 600/441 |
| 2012/0108971 A1 | 5/2012 | Miyama et al. | |
| 2013/0172755 A1 * | 7/2013 | Kim | G01S 15/8984 600/454 |
| 2014/0107484 A1 * | 4/2014 | Hyun | G06T 11/206 600/441 |
| 2014/0275976 A1 * | 9/2014 | Moro | A61B 5/029 600/419 |

* cited by examiner

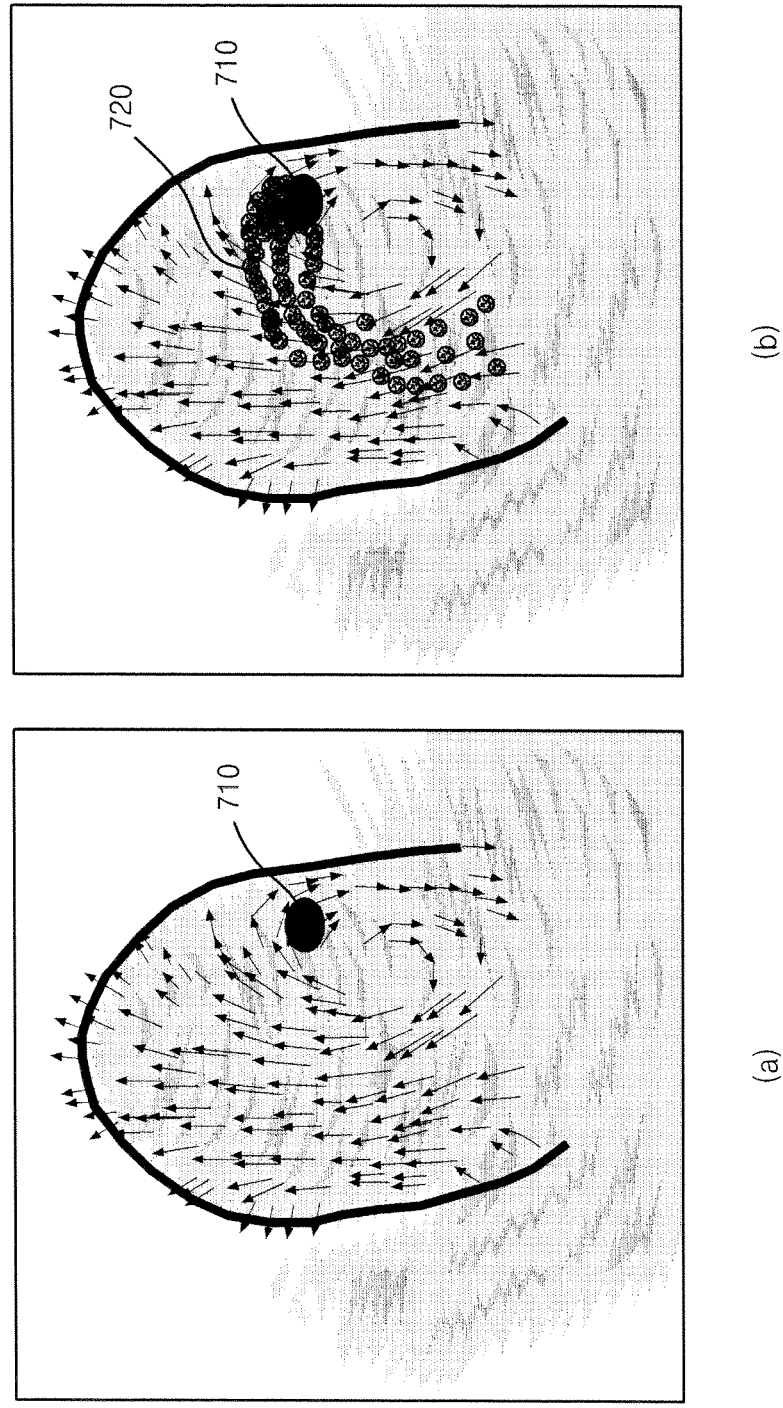

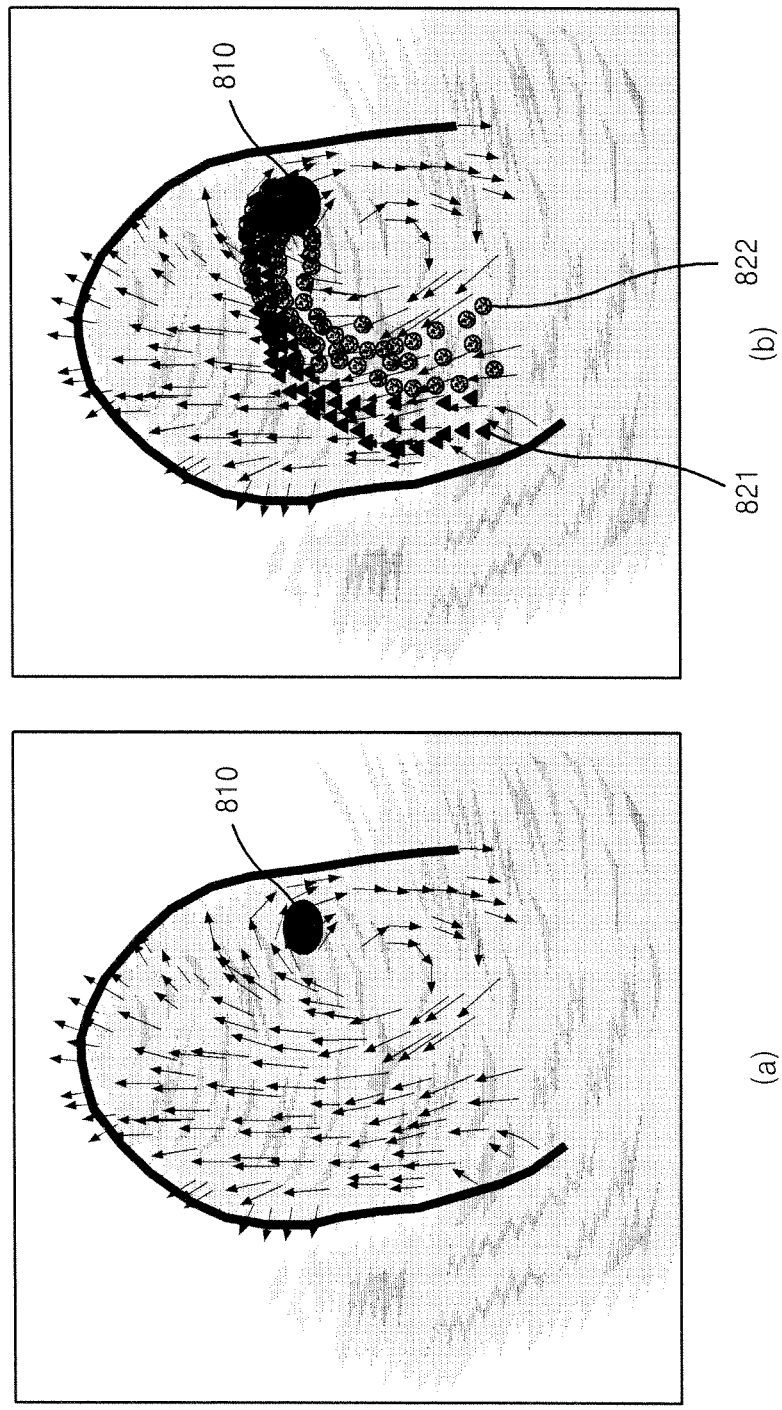

ULTRASOUND DIAGNOSTIC APPARATUS AND OPERATING METHOD THEREOF

RELATED APPLICATIONS

This application claims the benefit of Korean Patent Application No. 10-2014-0010885, filed on Jan. 28, 2014, in the Korean Intellectual Property Office, the disclosure of which is incorporated herein in its entirety by reference.

BACKGROUND

1. Field

One or more embodiments of the present invention relate to an ultrasound diagnostic apparatus and an operating method thereof, and more particularly, to an ultrasound diagnostic apparatus and an operating method thereof, which increase an accuracy of measurement for a flow of a moving object of interest (OOI).

2. Description of the Related Art

Ultrasound diagnostic apparatuses irradiate an ultrasound signal, generated from a transducer of a probe, onto an object and receive information of an echo signal reflected from the object, thereby obtaining an image of an internal part of the object. In particular, ultrasound diagnostic apparatuses are used for the medical purpose of observing the inside of an object, detecting a foreign material, and assessing an injury. Ultrasound diagnostic apparatuses have stabilities higher than those of diagnostic apparatuses using X-rays, display an image in real time, and are safe because there is no exposure to radioactivity, and thus may be widely used along with other image diagnostic apparatuses.

Ultrasound diagnostic apparatuses may provide a brightness (B) mode in which a reflection coefficient of an ultrasound signal reflected from an object is shown as a two-dimensional (2D) image, a Doppler mode image in which an image of a moving object (particularly, blood flow) is shown by using the Doppler effect, and an elastic mode image in which a reaction difference between when compression is applied to an object and when compression is not applied to the object is expressed as an image.

SUMMARY

One or more embodiments of the present invention include an ultrasound diagnostic apparatus and an operating method thereof, which measure and display a moving path of a moving OOI, thereby increasing an accuracy of a diagnosis of the moving OOI.

Additional aspects will be set forth in part in the description which follows and, in part, will be apparent from the description, or may be learned by practice of the presented embodiments.

According to one or more embodiments of the present invention, a method of operating an ultrasound diagnostic apparatus includes: displaying an ultrasound image of a target object; receiving an ultrasound signal obtained from a moving object of interest (OOI) included in the target object; setting a first reference region in the ultrasound image; acquiring first moving path information of the OOI passing through the first reference region, based on the received ultrasound signal; and displaying the first moving path in the ultrasound image, based on the first moving path information.

The setting of the first reference region may include setting, as the first reference region, at least one of a point, a line, and a region in the ultrasound image.

The method may further include: setting a second reference region in the ultrasound image; and acquiring second moving path information of the OOI passing through the second reference region, based on the received ultrasound signal, and displaying the second moving path to be identifiable from the first moving path, based on the second moving path information.

The displaying of the second moving path may include displaying the first and second moving paths in different colors.

The displaying of the second moving path may include, when the first and second moving paths overlap, displaying the overlapped region in a mixed color of a first color corresponding to the first moving path and a second color corresponding to the second moving path.

The displaying of the second moving path may include, when the first and second moving paths overlap, displaying a ratio of a volume of an OOI corresponding to the first moving path and a volume of an OOI corresponding to the second moving path, in the overlapped region.

The acquiring of the first moving path information may include tracing a moving path of the OOI flowing out from the first reference region to acquire the first moving path information.

The acquiring of the first moving path information may include reversely tracing a moving path of the OOI flowing into the first reference region to acquire the first moving path information.

The displaying of the first moving path may include displaying a start region of the first moving path.

According to one or more embodiments of the present invention, an ultrasound diagnostic apparatus includes: a display unit that displays an ultrasound image of a target object; an ultrasound signal receiving unit that receives an ultrasound signal obtained from a moving object of interest (OOI) included in the target object; a reference region setting unit that sets a first reference region in the ultrasound image; and a data processing unit that acquires first moving path information of the OOI passing through the first reference region, based on the received ultrasound signal, wherein the display unit displays the first moving path in the ultrasound image, based on the first moving path information.

The reference region setting unit may set, as the first reference region, at least one of a point, a line, and a region in the ultrasound image.

The reference region setting unit may set a second reference region in the ultrasound image, the data processing unit may acquire second moving path information of the OOI passing through the second reference region, based on the received ultrasound signal, and the display unit may display the second moving path to be identifiable from the first moving path, based on the second moving path information.

The display unit may display the first and second moving paths in different colors.

When the first and second moving paths overlap, the display unit may display the overlapped region in a mixed color of a first color corresponding to the first moving path and a second color corresponding to the second moving path.

When the first and second moving paths overlap, the display unit may display a ratio of a volume of an OOI corresponding to the first moving path and a volume of an OOI corresponding to the second moving path, in the overlapped region.

The data processing unit may trace a moving path of the OOI flowing out from the first reference region to acquire the first moving path information.

The data processing unit may reversely trace a moving path of the OOI flowing into the first reference region to acquire the first moving path information.

The display unit may display a start region of the first moving path.

BRIEF DESCRIPTION OF THE DRAWINGS

These and/or other aspects will become apparent and more readily appreciated from the following description of the embodiments, taken in conjunction with the accompanying drawings in which:

FIGS. 4 to 8 are diagrams referred to for describing the operating method of FIG. 3.

DETAILED DESCRIPTION

Figure 1:
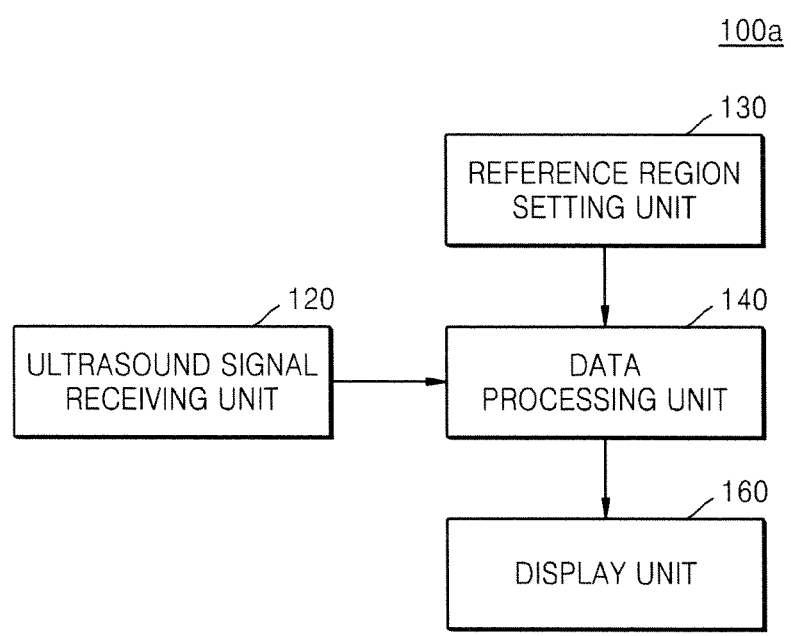
FIG. 1 is a block diagram illustrating a configuration of an ultrasound diagnostic apparatus according to an embodiment of the present invention.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. Expressions such as "at least one of," when preceding a list of elements, modify the entire list of elements and do not modify the individual elements of the list.

All terms including descriptive or technical terms which are used herein should be construed as having meanings that are obvious to one of ordinary skill in the art. However, the terms may have different meanings according to an intention of one of ordinary skill in the art, precedent cases, or the appearance of new technologies. Also, some terms may be arbitrarily selected by the applicant, and in this case, the meaning of the selected terms will be described in detail in the detailed description of the invention. Thus, the terms used herein have to be defined based on the meaning of the terms together with the description throughout the specification.

Also, when a part "includes" or "comprises" an element, unless there is a particular description contrary thereto, the part may further include other elements, not excluding the other elements. Moreover, each of terms such as ". . . unit" and "module" described in specification denotes an element for performing at least one function or operation, and may be implemented in hardware, software or a combination of hardware and software.

The term "ultrasound image" used herein denotes an image of an object acquired by using an ultrasound wave. Also, the term "object" used herein may include a person, an animal, a part of the person, or a part of the animal. For example, an object may include an organ such as a liver, a heart, a womb, a brain, breasts, an abdomen, or the like, or a blood vessel. Also, the term "object" may include a phantom. The phantom denotes a material having a volume that is very close to a density and effective atomic number of an organism, and may include a spherical phantom having a characteristic similar to a physical body.

Moreover, the ultrasound image may be implemented in various ways. For example, the ultrasound image may be at least one of an amplitude (A) mode image, a brightness (B) mode image, a color (C) mode image, and a Doppler (D) mode image. Also, according to an embodiment of the present invention, the ultrasound image may be a two-dimensional (2D) image or a three-dimensional (3D) image.

Moreover, the term "user" used herein is a medical expert, and may be a doctor, a nurse, a medical technologist, a medical image expert, or the like, or may be an engineer who repairs a medical apparatus. However, the user is not limited thereto.

The present invention will now be described more fully with reference to the accompanying drawings, in which exemplary embodiments of the invention are shown. The invention may, however, be embodied in many different forms and should not be construed as being limited to the embodiments set forth herein; rather, these embodiments are provided so that this disclosure will be thorough and complete, and will fully convey the concept of the invention to those of ordinary skill in the art. In the following description, well-known functions or constructions are not described in detail since they would obscure the invention with unnecessary detail. Throughout the specification, like reference numerals in the drawings denote like elements.

FIG. 1 is a block diagram illustrating a configuration of an ultrasound diagnostic apparatus 100a according to an embodiment of the present invention. Referring to FIG. 1, the ultrasound diagnostic apparatus 100a includes an ultrasound signal receiving unit 120, a reference region setting unit 130, a data processing unit 140, and a display unit 160.

The ultrasound diagnostic apparatus 100a may be implemented as a card type or a portable type. Examples of the ultrasound diagnostic apparatus 100a may include a picture archiving and communication system (PACS) viewer, a smartphone, a laptop computer, a personal digital assistant (PDA), and a tablet personal computer (PC), but are not limited thereto.

The ultrasound signal receiving unit 120 may process an echo signal received from a probe to generate ultrasound data. For example, the ultrasound signal receiving unit 120 may receive an echo signal obtained from a moving OOI included in a target object, and process the received echo signal to generate ultrasound data.

The reference region setting unit 130 may set a reference region in an ultrasound image. Also, the reference region setting unit 130 may set the reference region on the basis of a user input. For example, the reference region setting unit 130 may receive a user input that selects at least one of a point, a line, and a region in an ultrasound image, and set at least one of the selected point, line, and region as the reference region. Here, the user input may be input by using an input device such as a mouse, a keypad, or the like, and moreover, when the display unit 160 is configured with a touch screen, the user input may be a touch input that is input by using a touch tool (for example, a finger, an electronic pen, or the like).

Moreover, the reference region setting unit 130 may set a plurality of reference regions, and the set reference regions may be displayed in a color.

The data processing unit 140 may acquire moving path information of an OOI passing through the reference region which is set by the reference region setting unit 130, on the basis of the received ultrasound signal. Also, when the reference region is set in plurality, the data processing unit 140 may acquire moving path information of an OOI passing through each of the plurality of reference regions.

The data processing unit 140 may trace a moving path of an OOI flowing out from the reference region, or may reversely trace a moving path of an OOI flowing into the reference region, thereby acquiring moving path information.

The display unit 160 displays the ultrasound image generated by the image generating unit 155. The display unit 160 may display various pieces of information processed by the ultrasound diagnostic apparatus 100, in addition to the ultrasound image, on a screen through a graphics user interface (GUI). The ultrasound diagnostic apparatus 100 may include two or more display units 160 depending on an implementation type.

The display unit 160 includes at least one of a liquid crystal display (LCD), a thin film transistor-liquid crystal display (TFT-LCD), an organic light-emitting diode (OLED), a flexible display, a 3D display, and an electrophoretic display.

Moreover, when the display unit 160 and the user input unit 190 are implemented as a touch screen by forming a layer structure, the display unit 160 may be used as an input unit that enables information to be input by a user's touch, in addition to an output unit.

The touch screen may be configured to detect a touch pressure in addition to a touch input position and a touched area. Also, the touch screen may be configured to detect a proximity touch as well as a real touch.

Herein, the term "real touch" denotes a case in which a pointer really touches a screen, and the term "proximity touch" denotes a case in which the pointer does not actually touch the screen but approaches a position which is separated from the screen by a certain distance. The pointer used herein denotes a touch instrument for really touching or proximity-touching a specific portion of a displayed screen. Examples of the pointer include an electronic pen, a finger, etc.

Although not shown, the ultrasound diagnostic apparatus 100 may include various sensors inside or near the touch screen, for detecting a real touch or a proximity touch on the touch screen. An example of a sensor for sensing a touch of the touch screen is a tactile sensor.

The tactile sensor denotes a sensor that senses a touch by a specific object to a degree to which a user feels, or more. The tactile sensor may sense various pieces of information such as a roughness of a touched surface, a stiffness of a touched object, a temperature of a touched point, etc.

Moreover, an example of a sensor for sensing a touch of the touch screen is a proximity sensor. The proximity sensor denotes a sensor that detects an object approaching a detection surface or an object near the detection surface by using an electromagnetic force or infrared light without any mechanical contact.

Examples of the proximity sensor include a transmissive photosensor, a directly reflective photosensor, a mirror reflective photosensor, a high frequency oscillation-type proximity sensor, a capacitive proximity sensor, a magnetic proximity sensor, and an infrared proximity sensor.

The display unit 160 according to an embodiment of the present invention may display an ultrasound image of a target object, and display the moving path of the OOI on the basis of the moving path information of the OOI acquired by the data processing unit 140.

Moreover, the display unit 160 may display the reference region set by the reference region setting unit 130, and when a plurality of moving paths are acquired, the display unit 160 may identifiably display the plurality of moving paths. In this case, the moving paths may be displayed in different colors.

Moreover, when the plurality of moving paths overlap, the display unit 160 may display the overlapped regions in a mixed color of colors which respectively correspond to the plurality of moving paths. For example, when first and second moving paths overlap, the display unit 160 may display the overlapped region in a mixed color of first and second colors which respectively correspond to the first and second moving paths.

Moreover, the display unit 160 may display, in the overlapped region, a ratio of a volume of an OOI (corresponding to the first moving path) and a volume of an OOI corresponding to the second moving path.

Figure 2:
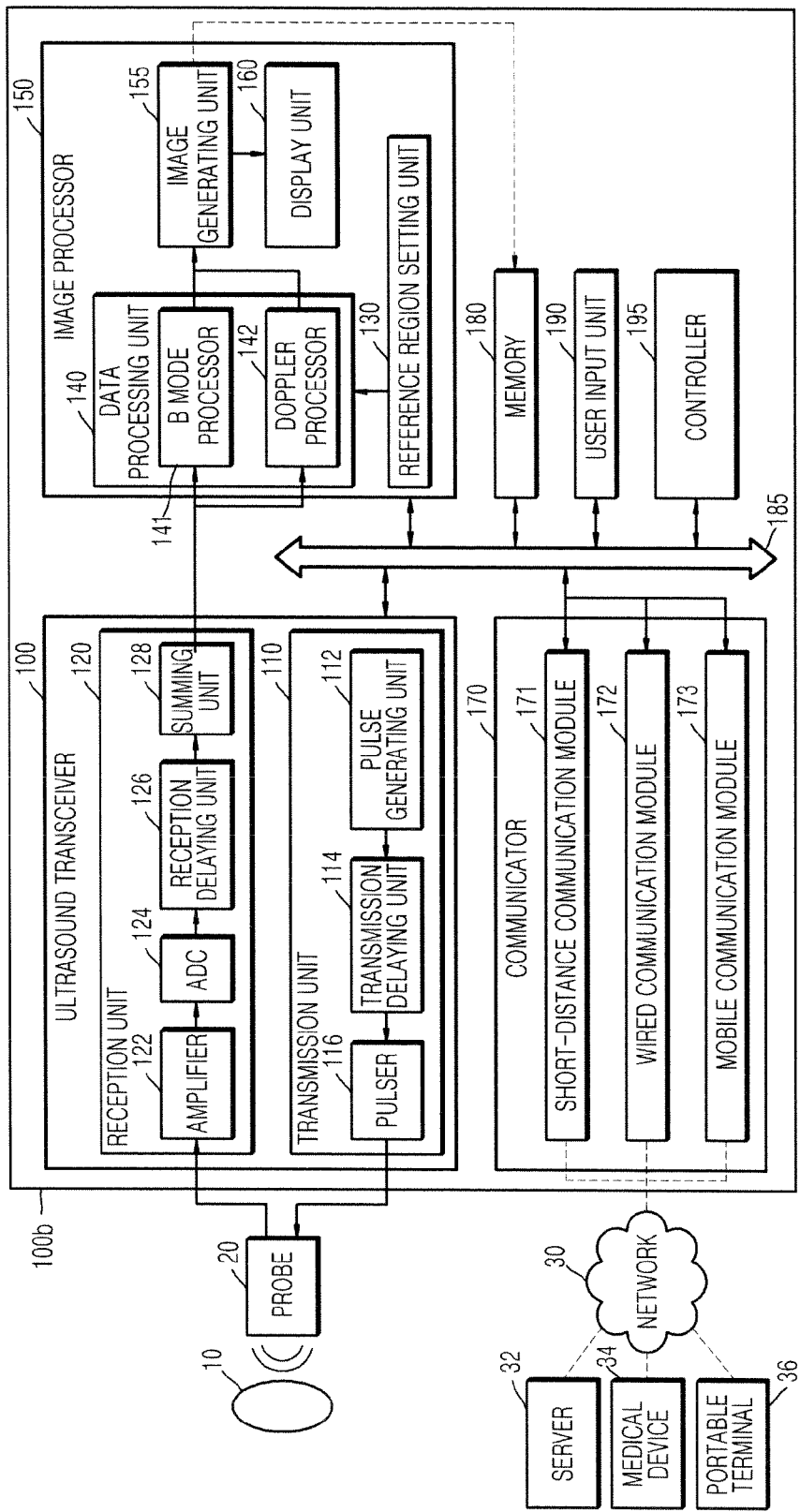
FIG. 2 is a block diagram illustrating a configuration of an ultrasound diagnostic apparatus according to an embodiment of the present invention.

FIG. 2 is a block diagram illustrating a configuration of an ultrasound diagnostic apparatus 100b according to an embodiment of the present invention. Referring to FIG. 2, the ultrasound diagnostic apparatus 100b according to an embodiment of the present invention includes a probe 20, an ultrasound transceiver 100, an image processor 150, a communicator 170, a memory 180, a user input unit 190, and a controller 195. The above-described elements may be connected to each other through a bus 185.

An ultrasound receiver 120, data processing unit 140, a reference region setting unit 130, and display unit 160 of FIG. 2 are the same elements as the ultrasound signal receiving unit 120, data processing unit 140, reference region setting unit 130, and display unit 160 of FIG. 1, respectively, and the descriptions of FIG. 1 are applied thereto.

The probe 20 transmits ultrasound waves to an object 10 based on a driving signal applied by the ultrasound transceiver 100 and receives echo signals reflected by the object 10. The probe 20 includes a plurality of transducers, and the plurality of transducers oscillate based on electric signals transmitted thereto and generate acoustic energy, that is, ultrasound waves. Furthermore, the probe 20 may be connected to the main body of the ultrasound diagnostic apparatus 100b by wire or wirelessly. According to embodiments of the present invention, the ultrasound diagnostic apparatus 100b may include a plurality of probes 20.

A transmission unit 110 supplies a driving signal to the probe 20 and includes a pulse generating unit 112, a transmission delaying unit 114, and a pulser 116. The pulse generating unit 112 generates pulses for forming transmission ultrasound waves based on a predetermined pulse repetition frequency (PRF), and the transmission delaying unit 114 applies a delay time for determining transmission directionality to the pulses. Pulses to which a delay time is applied correspond to a plurality of piezoelectric vibrators included in the probe 20, respectively. The pulser 116 applies a driving signal (or a driving pulse) to the probe 20 as a timing corresponding to each pulse to which a delay time is applied.

A reception unit 120 generates ultrasound data by processing echo signals received from the probe 20 and may include an amplifier 122, an analog-digital converter (ADC) 124, a reception delaying unit 126, and a summing unit 128. The amplifier 122 amplifies echo signals in each channel, and the ADC 124 analog-to-digital converts the amplified echo signals. The reception delaying unit 126 applies delay times for determining reception directionality to the digital-converted echo signals, and the summing unit 128 generates ultrasound data by summing the echo signals processed by the reception delaying unit 126.

The image processor 150 generates an ultrasound image by scan-converting ultrasound data generated by the ultrasound transceiver 100 and displays the ultrasound image.

An ultrasound image may include not only a grayscale ultrasound image obtained by scanning an object in an amplitude (A) mode, a brightness (B) mode, and a motion (M) mode, but also a blood flow Doppler image showing flow of blood (also referred to as a color Doppler image), a tissue Doppler image showing movement of tissues, and a spectral Doppler image showing moving speed of an object as a waveform.

A B mode processor 141 extracts B mode components from ultrasound data and processes the B mode components. An image generating unit 155 may generate an ultrasound image indicating signal intensities as brightness based on the extracted B mode components.

Similarly, a Doppler processor 142 may extract Doppler components from ultrasound data, and the image generating unit 155 may generate a Doppler image indicating movement of an object as colors or waveforms based on the extracted Doppler components.

The image generating unit 155 according to an embodiment of the present invention may generate a 3D ultrasound image via volume-rendering of volume data and may also generate an elasticity image which visualizes deformation of an object 10 due to pressure. Furthermore, the image generating unit 155 may mark various pieces of additional information on an ultrasound image by using texts and graphics. The generated ultrasound image may be stored in the memory 180.

The communicator 170 is connected to a network 30 in a wired or wireless manner to communicate with an external device or server. The communicator 170 may exchange data with a hospital server or a medical apparatus of a hospital which is connected thereto through a medical image information system (a PACS). Also, the communicator 170 may perform data communication according to the digital imaging and communications in medicine (DICOM) standard.

The communicator 170 may transmit and receive data, such as an ultrasound image, ultrasound data, Doppler data, etc. of an object, associated with a diagnosis of the object over the network 30, and may also transmit and receive a medical image captured by a medical apparatus such as a computed tomography (CT) apparatus, a magnetic resonance imaging (MRI) apparatus, or an X-ray apparatus. Furthermore, the communicator 170 may receive information on a diagnosis history or treatment schedule of a patient from a server, and use a diagnosis of an object. In addition, the communicator 170 may perform data communication with a portable terminal of a doctor or a patient, in addition to a server or medical apparatus of a hospital.

The communicator 170 may be connected to the network 30 in a wired or wireless manner, and may exchange data with a server 32, a medical apparatus 34, or a portable terminal 36. The communicator 170 may include one or more elements that enable communication with an external device, and for example, include a short-distance communication module 171, a wired communication module 172, and a mobile communication module 173.

The short-distance communication module 171 denotes a module for short-distance communication within a certain distance. Short-distance communication technology, according to an embodiment of the present invention, may include wireless LAN, Wi-Fi, Bluetooth, Zigbee, Wi-Fi direct (WFD), ultra wideband (UWB), infrared data association (IrDA), Bluetooth low energy (BLE), and near field communication (NFC), but the short-distance communication technology is not limited thereto.

The wired communication module 172 denotes a module for communication using an electrical signal or an optical signal. Wired communication technology according to an embodiment may include a pair cable, a coaxial cable, an optical fiber cable, or an Ethernet cable.

The mobile communication module 173 transmits and receives a radio frequency (RF) signal to and from a base station, an external terminal, and a server over a mobile communication network. Here, the RF signal may include various types of data based on transmission and reception of a voice call signal, a video call signal, or a letter/multimedia message.

The memory 180 stores various pieces of information processed by the ultrasound diagnostic apparatus 100b. For example, the memory 180 may store medical data, such as input/output ultrasound data and ultrasound images, associated with a diagnosis of an object, and may also store an algorithm or a program which is executed in the ultrasound diagnostic apparatus 100b.

The memory 180 may be configured with various kinds of storage mediums such as a flash memory, a hard disk, an EEPROM, etc. Also, the ultrasound diagnostic apparatus 100b may operate web storage or a cloud server which performs a storage function of the memory 180 on a web.

The user input unit 190 generates input data which is input by a user for controlling an operation of the ultrasound diagnostic apparatus 100b. The user input unit 190 may include hardware elements such as a keypad, a mouse, a touch pad, a trackball, a jog switch, but is not limited thereto. As another example, the user input unit 190 may further include various sensors such as an electrocardiogram (ECG) measurement module, a breath measurement sensor, a voice recognition sensor, a gesture recognition sensor, a fingerprint recognition sensor, an iris recognition sensor, a depth sensor, a distance sensor, etc.

In particular, the user input unit 190 may further include the touch screen in which the touch pad and the display unit 160 form the layer structure.

In this case, the ultrasound diagnostic apparatus 100b may display a specific mode ultrasound image and a control panel for an ultrasound image, on the touch screen. In addition, the ultrasound diagnostic apparatus 100b may sense a user's touch gesture for an ultrasound image through the touch screen.

The ultrasound diagnostic apparatus 100b according to an embodiment of the present invention may physically include some buttons, frequently used by a user, from among a plurality of buttons included in a control panel of general ultrasound diagnostic apparatuses, and the other buttons may be provided through a type of GUI on the touch screen.

The controller 195 controls an overall operation of the ultrasound diagnostic apparatus 100b. That is, the controller 195 may control operations between the probe 20, the ultrasound transceiver 100, the image processor 150, the communicator 170, the memory 180, and the user input unit 190 which are illustrated in FIG. 2.

Some or all of the probe 20, the ultrasound transceiver 100, the image processor 150, the communicator 170, the memory 180, the user input unit 190, and the controller 195 may be operated by a software module, but are not limited thereto. Some of the above-described elements may be operated by a hardware module. Also, at least some of the ultrasound transceiver 100, the image processor 150, and the communicator 170 may be included in the controller 195, but are not limited to the implementation type.

The block diagram of each of the ultrasound diagnostic apparatuses 100a and 100b of FIGS. 1 and 2 is a block diagram according to an embodiment of the present invention. The elements of the block diagram may be integrated, added, or omitted depending on a specification of an actually implemented cache memory system. That is, depending on the case, two or more elements may be integrated into one element, or one element may be subdivided into two or more elements. Also, a function performed by each element is for describing an embodiment of the present invention, and each element or a detailed operation thereof does not limit the scope and spirit of the present invention.

Figure 3:
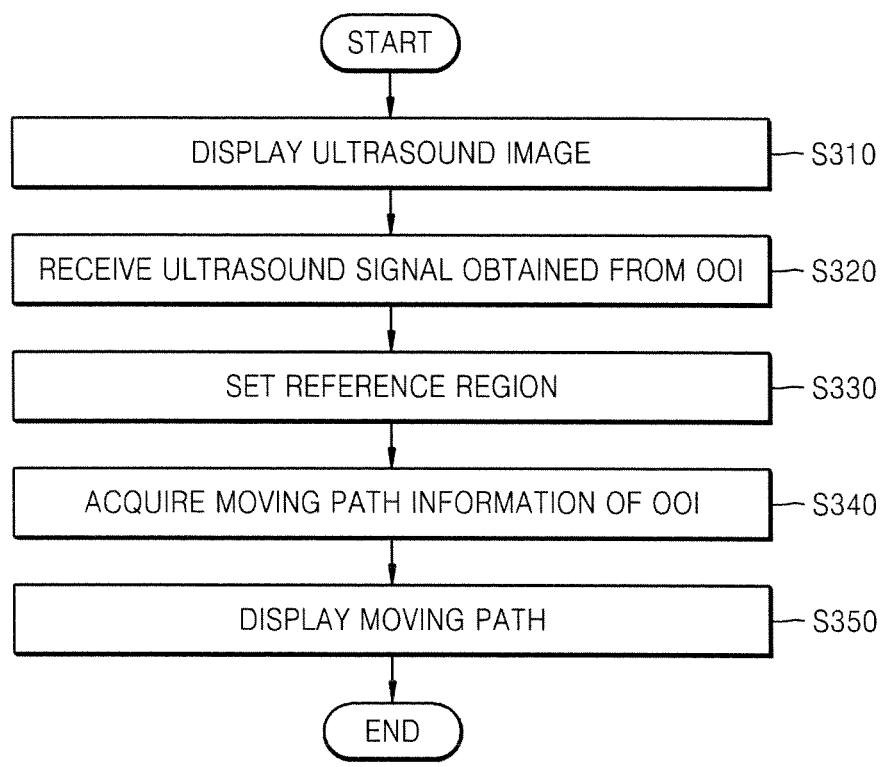
FIG. 3 is a flowchart illustrating a method of operating an ultrasound diagnostic apparatus according to an embodiment of the present invention.

FIG. 3 is a flowchart illustrating a method of operating an ultrasound diagnostic apparatus according to an embodiment of the present invention.

Referring to FIG. 3, the ultrasound diagnostic apparatus 100a (100b) may display an ultrasound image of an object in operation S310.

In this case, the object may be a heart, but is not limited thereto. Also, the ultrasound diagnostic apparatus 100a (100b) may set a region of interest (ROI) in the ultrasound image. For example, the ultrasound diagnostic apparatus 100a (100b) may generate the ultrasound image of the object on the basis of acquired ultrasound data, and display the ultrasound image in the display unit 160.

For example, as illustrated in FIG. 4(a), when the ultrasound image of the object is displayed, the ultrasound diagnostic apparatus 100a (100b) may set a boundary 415 of the ROI. Here, the boundary 415 of the ROI may be set according to a user input.

Moreover, when the ROI may be set due to the boundary 415, the ultrasound diagnostic apparatus 100a (100b) may perform, in only the set ROI, a below-described operation of tracing a moving path of an OOI.

In operation S320, the ultrasound diagnostic apparatus 100a (100b) may receive an ultrasound signal obtained from a moving OOI included in a target object.

Here, the moving OOI may be blood flow, but is not limited thereto. The ultrasound diagnostic apparatus 100a (100b) may track a contrast medium injected into the target object to receive the ultrasound signal obtained from the moving OOI. Alternatively, the ultrasound diagnostic apparatus 100a (100b) may receive a Doppler signal obtained from the moving OOI.

In operation S330, the ultrasound diagnostic apparatus 100a (100b) may set a first reference region included in the ultrasound image.

Here, the first reference region may be at least one of a point, a line, and a region.

For example, referring to FIG. 4(a), an input for selecting the first reference region may be an input that selects a first point 410 of the ultrasound image.

The first point 410 may be automatically selected by the ultrasound diagnostic apparatus 100a (100b), or may be selected based on a user input. For example, a user may select a reference point for acquiring a moving path of an OOI by using an input device, such as a mouse or a keypad, or a touch tool (for example, a finger, an electronic pen, or the like).

Referring to FIG. 5(a), the input for selecting the first reference region may be an input that selects lines 510, 520 and 530 in the ultrasound image.

Moreover, although not shown, the ultrasound diagnostic apparatus 100a (100b) may select a certain region of an ROI, and analyze a moving path of an OOI, flowing out from the selected region, or a moving path of an OOI flowing into the selected region.

The selected point, line, and region may be displayed in a color on the ultrasound image, and the color may be set by the user.

Moreover, each of the point, line, and region may be selected in plurality, and may be displayed in different colors. For example, as illustrated in FIG. 5(a), when three lines 510, 520 and 530 are selected, a first line 510 may be displayed in a first color (illustrated as a triangle in FIG. 5(a)), a second line 520 may be displayed in a second color (illustrated as a circle in FIG. 5(a)), and a third line 530 may be displayed in a third color (illustrated as a diamond in FIG. 5(a)).

In operation S340, the ultrasound diagnostic apparatus 100a (100b) may acquire first moving path information of an OOI passing through the first reference region, on the basis of the received ultrasound signal.

The ultrasound diagnostic apparatus 100a (100b) may acquire moving path information of a moving OOI included in a target object, on the basis of an ultrasound signal. For example, the ultrasound diagnostic apparatus 100a (100b) may inject a contrast medium into the target object, and track the injected contrast medium, thereby acquiring information (including a velocity, a moving direction, etc. of the OOI) about the moving OOI in an ROI. Alternatively, the ultrasound diagnostic apparatus 100a (100b) may extract a Doppler component from ultrasound data of the target objet, and acquire information (including a velocity, a moving direction, etc. of the OOI) about the moving OOI included in the target object on the basis of the extracted Doppler component.

Figure 4:
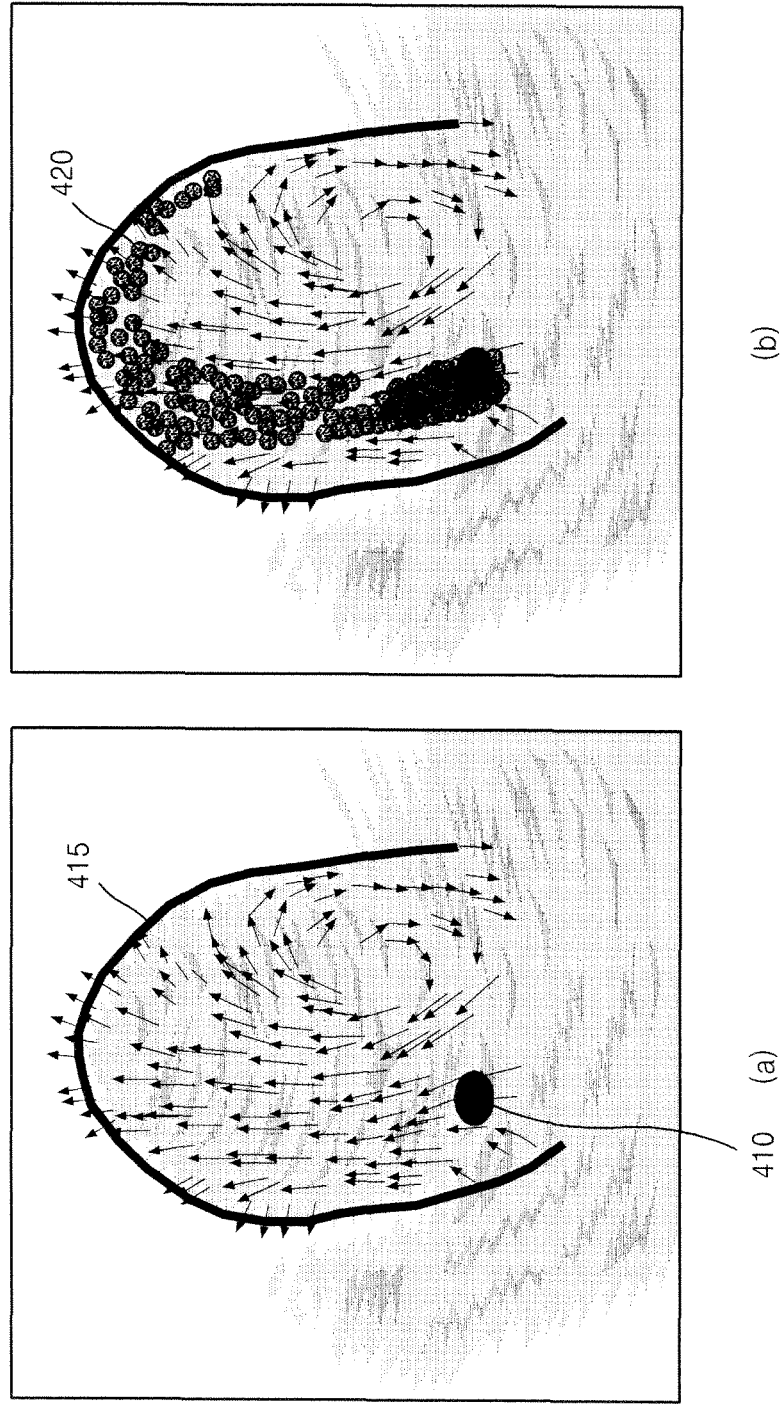
Figure 5:
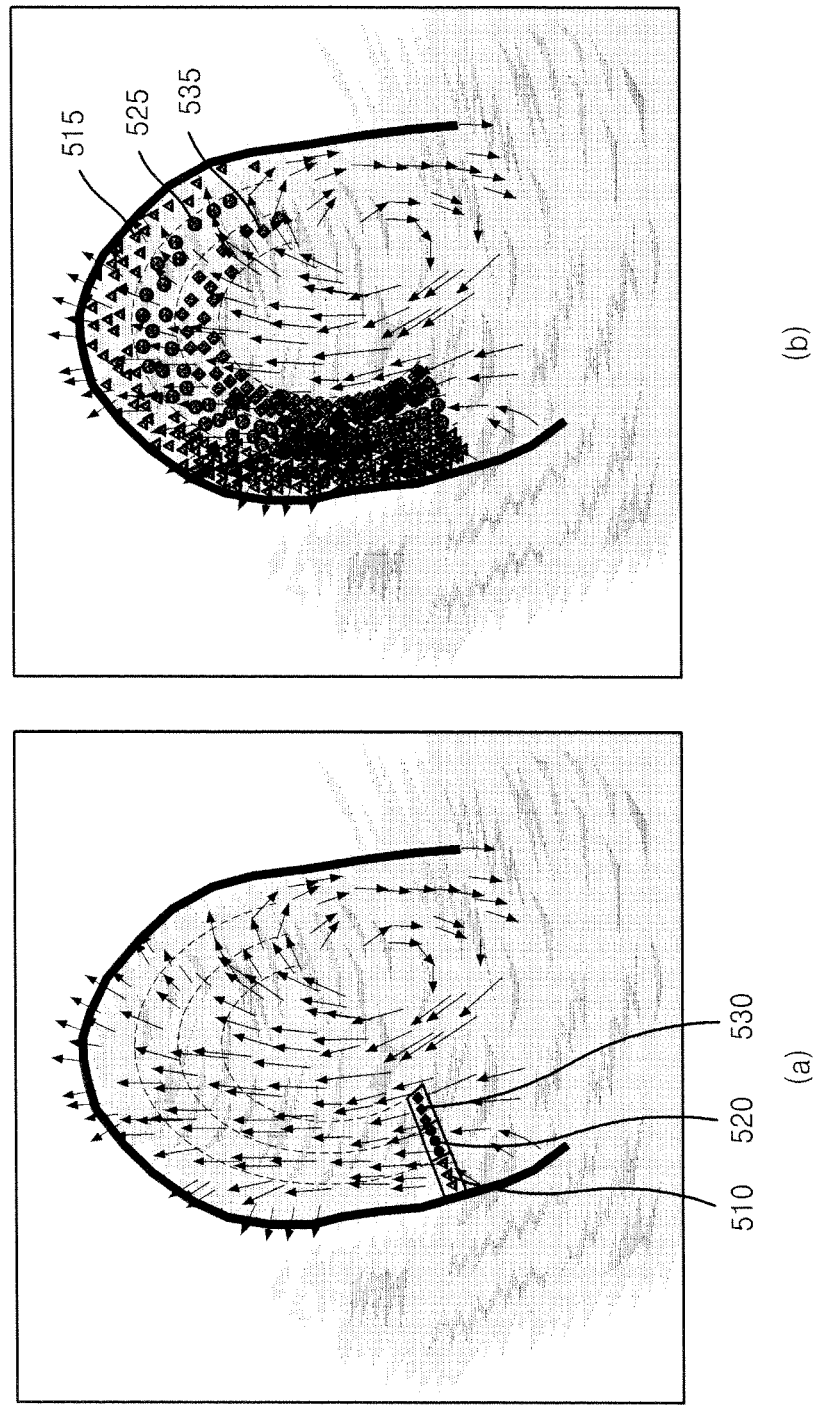

The ultrasound diagnostic apparatus 100a (100b), as illustrated in FIGS. 4 and 5, may display a moving OOI in an ROI as a type of a vector (for example, an arrow) having a size and direction of a velocity on the basis of information (which is acquired as described above) about the moving OOI.

Moreover, the ultrasound diagnostic apparatus 100a (100b) may acquire moving path information of an OOI passing through a set reference region.

As illustrated in FIG. 4(a), when a first point 410 of an ultrasound image is set as a reference region, the ultrasound diagnostic apparatus 100a (100b) may acquire a moving path of a moving OOI with respect to the first point 410.

For example, the ultrasound diagnostic apparatus 100a (100b) may trace a moving path of an OOI flowing out from the first point 410 to acquire moving path information, based on movement information of the OOI.

In S350, the ultrasound diagnostic apparatus 100a (100b) may display the acquired moving path.

For example, as illustrated in FIG. 4(b), the ultrasound diagnostic apparatus 100a (100b) may display a moving path 420 of the OOI flowing out from the first point 410 on the basis of the acquired moving path information.

In this case, the moving path (a diffusion path) of the OOI may be displayed in a color, which may be set by a user input. Also, a concentration of the color may be changed according to a volume of the OOI. That is, a region where the volume of the OOI is high may be displayed in a deep color, and a region where the volume of the OOI is low may be displayed in a deep color.

Moreover, when a volume of an OOI that moves a first direction is less than a predetermined threshold value, a moving path through which the OOI moves in the first direction may not be displayed. That is, only a main moving path of the OOI may be displayed.

As described above, since the moving path of the OOI flowing out from the first point 410 is displayed, a user easily determines a part of an ROI that is affected by the OOI flowing out from the first point 410.

FIGS. 5(a) and (b) are diagrams illustrating a case in which a plurality of lines in an ultrasound image are set as reference regions.

Referring to FIG. 5(a), the ultrasound diagnostic apparatus 100a (100b) may set a plurality of lines as reference regions. Here, the set plurality of reference regions (the plurality of lines) may be displayed in different colors.

As illustrated in FIG. 5(a), when the lines 510, 520 and 530 are set as reference regions, the first line 510 may be displayed in the first color (illustrated as a triangle in FIG. 5(a)), the second line 520 may be displayed in the second color (illustrated as a circle in FIG. 5(a)), and the third line 530 may be displayed in the third color (illustrated as a diamond in FIG. 5(a)).

The ultrasound diagnostic apparatus 100a (100b) may acquire a moving path of a moving OOI with respect to the first to third lines 510, 520 and 530. For example, as illustrated in FIG. 5(b), the ultrasound diagnostic apparatus 100a (100b) may trace a moving path of an OOI flowing out from a region corresponding to the first line 510 to acquire a moving path 515, based on movement information of the OOI, and display the acquired moving path 515.

Moreover, the ultrasound diagnostic apparatus 100a (100b) may trace a moving path of an OOI flowing out from a region corresponding to the second line 520 to acquire a moving path 525, and display the acquired moving path 525. In addition, the ultrasound diagnostic apparatus 100a (100b) may trace a moving path of an OOI flowing out from a region corresponding to the third line 530 to acquire a moving path 535, and display the acquired moving path 535.

In this case, the moving path of each of the OOIs may be displayed in a color corresponding to a corresponding reference region. For example, a moving path (the first moving path 515) of an OOI flowing out from the first line 510 may be displayed in the first color (illustrated as a triangle in FIG. 5(b)), a moving path (the second moving path 525) of an OOI flowing out from the second line 520 may be displayed in the second color (illustrated as a circle in FIG. 5(b)), and a moving path (the third moving path 535) of an OOI flowing out from the third line 530 may be displayed in the third color (illustrated as a diamond in FIG. 5(b)).

Moreover, as described above with reference to FIG. 4, a concentration of the color may be changed according to a volume of the OOI. That is, a region where the volume of the OOI is high may be displayed in a deep color, and a region where the volume of the OOI is low may be displayed in a deep color.

Moreover, when the moving path (the first moving path 515) of the OOI flowing out from the first line 510 overlaps the moving path (the second moving path 525) of the OOI flowing out from the second line 520, the overlapped region may be displayed in a mixed color of the first and second colors. For example, when the first color is red and the second color is yellow, the ultrasound diagnostic apparatus 100a (100b) may display the overlapped region in an orange color.

Moreover, the ultrasound diagnostic apparatus 100a (100b) may display a volume of an OOI in an overlapped region. For example, in a region where the first and second moving paths overlap, the ultrasound diagnostic apparatus 100a (100b) may display, as numerical values, a volume of an OOI having the first moving path 515 and a volume of an OOI having the second moving path 525, or the ultrasound diagnostic apparatus 100a (100b) may display a ratio of the volumes as a numerical value.

Alternatively, a mixed color of an overlapped region may be changed based on the ratio of the volume of the OOI having the first moving path 515 and the volume of the OOI having the second moving path 525. For example, when the volume of the OOI having the first moving path 515 is greater than the volume of the OOI having the second moving path 525, the overlapped region may be displayed in a mixed color in which a mixing ratio of the first color is higher than that of the second color.

The ultrasound diagnostic apparatus 100a (100b) may display a 3D ultrasound image, set a certain region of the 3D ultrasound image as a reference region, and acquire a moving path of an OOI passing through the set reference region.

Figure 6:
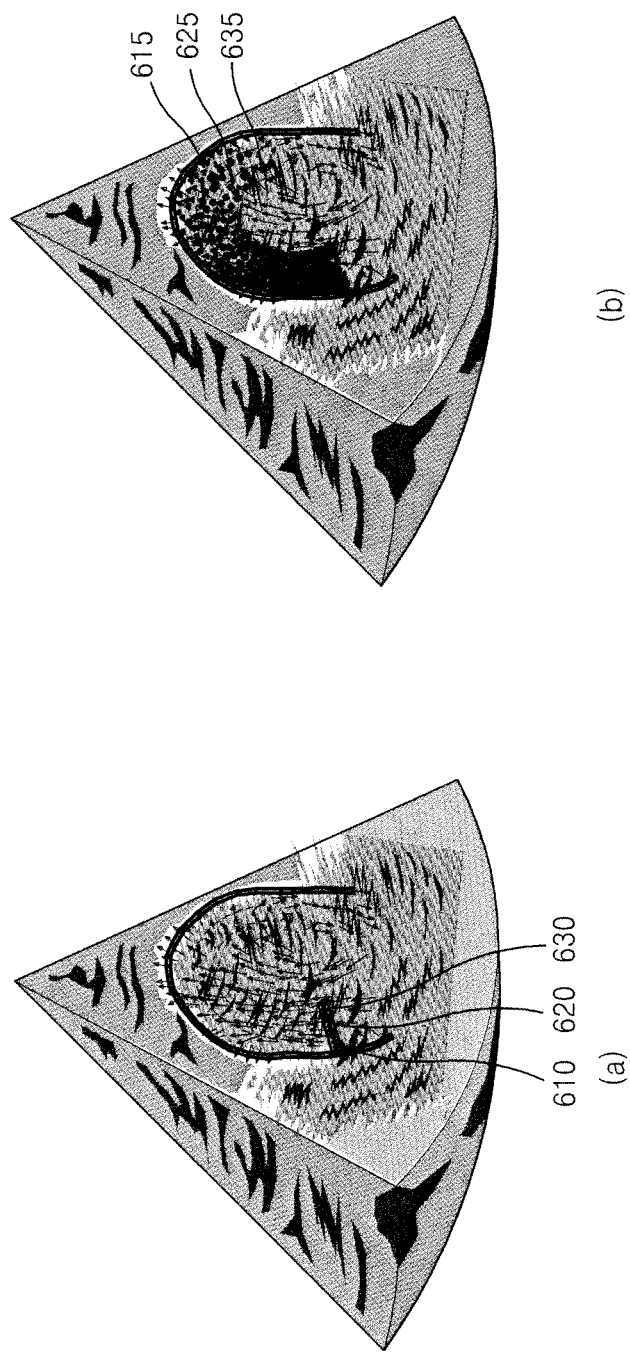

Referring to FIG. 6(a), the ultrasound diagnostic apparatus 100a (100b) may set a plurality of regions as reference regions. Here, the plurality of regions may be a point, a line, and a region, and may be displayed in different colors.

For example, as illustrated in FIG. 6(a), first to third regions 610, 620 and 630 may be displayed in different colors.

The ultrasound diagnostic apparatus 100a (100b) may acquire a moving path of a moving OOI with respect to each of the plurality of regions. For example, as illustrated in FIG. 6(b), the ultrasound diagnostic apparatus 100a (100b) may trace a moving path of an OOI flowing out from each region to acquire moving paths 615, 625 and 635, based on movement information of the OOI, and display the acquired moving paths 615, 625 and 635.

In this case, each of the moving paths 615, 625 and 635 of the OOIs may be displayed in a color corresponding to a corresponding reference region, and a concentration of the color may be changed based on a volume of a corresponding OOI. Also, when the moving paths overlap, the overlapped region may be displayed in a mixed color of colors of the moving paths.

The ultrasound diagnostic apparatus 100a (100b) may reversely trace a moving path of a moving OOI with respect to a set reference region (for example, a point, a line, or a region).

As illustrated in FIG. 7(a), when a second point 710 in an ultrasound image is selected, the ultrasound diagnostic apparatus 100a (100b) may reversely trace a moving path of a moving OOI with respect to the second point 710. For example, as illustrated in FIG. 7(b), the ultrasound diagnostic apparatus 100a (100b) may reversely trace a moving path of an OOI flowing out from the second point 710 on the basis of movement information of the OOI, and display the traced moving path 720.

In this case, the moving path 720 of the OOI may be displayed in a color, which may be set by a user input. Also, a concentration of the color may be changed according to a volume of the OOI. That is, a region where the volume of the OOI is high may be displayed in a deep color, and a region where the volume of the OOI is low may be displayed in a deep color.

As described above, since the moving path 720 of the OOI flowing into the second point 710 is displayed, a user easily determines which region of a target object the OOI flowing into the second point 710 reaches the second point 710 via.

Moreover, as illustrated in FIG. 8, when a moving path of an OOI flowing into a second point 810 is provided in plurality, the ultrasound diagnostic apparatus 100a (100b)

may display moving paths 821 and 822. Here, the moving paths 821 and 822 may be displayed in different colors, and colors of the moving paths 821 and 822 may be set according to a user input. For example, a first moving path 821 may be displayed in the first color (illustrated as a triangle in FIG. 8(*b*)), and a second moving path 822 may be displayed in the second color (illustrated as a circle in FIG. 8(*b*)).

Moreover, when the first moving path 821 of an OOI flowing into the second point 810 overlaps the moving path 822 (which differs from the first moving path) of the OOI flowing into the second point 810, the ultrasound diagnostic apparatus 100*a* (100*b*) may display the overlapped region in a mixed color of the first and second colors. For example, when the first color is red and the second color is yellow, the ultrasound diagnostic apparatus 100*a* (100*b*) may display the overlapped region in an orange color.

Moreover, the ultrasound diagnostic apparatus 100*a* (100*b*) may display a volume of an OOI in an overlapped region. For example, in a region where the first and second moving paths overlap, the ultrasound diagnostic apparatus 100*a* (100*b*) may display, as numerical values, a volume of an OOI having the first moving path and a volume of an OOI having the second moving path, or the ultrasound diagnostic apparatus 100*a* (100*b*) may display a ratio of the volumes as a numerical value.

Alternatively, a mixed color of an overlapped region may be changed based on the ratio of the volume of the OOI having the first moving path and the volume of the OOI having the second moving path. For example, when the volume of the OOI having the first moving path is greater than the volume of the OOI having the second moving path, the overlapped region may be displayed in a mixed color in which a mixing ratio of the first color is higher than that of the second color.

As described above, according to the one or more of the above embodiments of the present invention, by displaying a moving path of an OOI passing through a reference region, a user easily determines the moving path of the OOI passing through the reference region.

Moreover, the user quickly determines a part affected by the OOI.

Therefore, an accuracy of a diagnosis of the OOI increases.

The ultrasound diagnostic apparatus and the operating method thereof according to embodiments of the present invention may also be embodied as computer readable codes on a computer readable recording medium. The computer readable recording medium is any data storage device that can store data which can be thereafter read by a computer system. Examples of the computer readable recording medium include read-only memory (ROM), random-access memory (RAM), CD-ROMs, magnetic tapes, floppy disks, and optical data storage. The computer readable recording medium can also be distributed over network coupled computer systems so that the computer readable code may be stored and executed in a distributed fashion.

It should be understood that the exemplary embodiments described herein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

What is claimed is:

1. A method of operating an ultrasound diagnostic apparatus, the method comprising:
   displaying, on a display of the ultrasound diagnostic apparatus, an ultrasound image of a target object;
   receiving, through an ultrasound probe of the ultrasound diagnostic apparatus, an ultrasound signal obtained from a moving object of interest (OOI) included in the target object;
   setting, by a processor of the ultrasound diagnostic apparatus, a first reference region and a second reference region in the ultrasound image;
   acquiring, by the processor of the ultrasound diagnostic apparatus, first moving path information of the OOI passing through the first reference region and second moving path information of the OOI passing through the second reference region, based on the ultrasound signal received through the ultrasound probe;
   generating, by the processor of the ultrasound diagnostic apparatus, and displaying, on the display of the ultrasound diagnostic apparatus, an ultrasound image including the first moving path, based on the first moving path information acquired based on the ultrasound signal received through the ultrasound probe; and
   generating, by the processor of the ultrasound diagnostic apparatus, and displaying, on the display of the ultrasound diagnostic apparatus, the second moving path to be identifiable from the first moving path, based on the second moving path information,
   wherein the generating and displaying the second moving path comprises, when the first and second moving paths overlap, generating and displaying a ratio of a volume of an OOI corresponding to the first moving path and a volume of an OOI corresponding to the second moving path, in the overlapped region.

2. The method of claim 1, wherein the setting of the first reference region comprises setting, as the first reference region, at least one of a point, a line, and a region in the ultrasound image.

3. The method of claim 1, wherein the displaying of the second moving path comprises displaying the first and second moving paths in different colors.

4. The method of claim 3, wherein the displaying of the second moving path comprises, when the first and second moving paths overlap, displaying the overlapped region in a mixed color of a first color corresponding to the first moving path and a second color corresponding to the second moving path.

5. The method of claim 1, wherein the acquiring of the first moving path information comprises tracing a moving path of the OOI flowing out from the first reference region to acquire the first moving path information.

6. The method of claim 1, wherein the acquiring of the first moving path information comprises tracing a moving path of the OOI flowing into the first reference region from at least one other region in the ultrasound image to acquire the first moving path information.

7. The method of claim 6, wherein the displaying of the first moving path comprises displaying a start region of the first moving path.

8. An ultrasound diagnostic apparatus comprising:
   a display configured to display an ultrasound image of a target object;

a probe configured to receive an ultrasound signal obtained from a moving object of interest (OOI) included in the target object; and at least one processor configured to:
set a first reference region and a second reference region in the ultrasound image,
acquire first moving path information of the OOI passing through the first reference region and second moving path information of the OOI passing through the second reference region, based on the ultrasound signal received through the probe,
generate and display on the display an ultrasound image including the first moving path, based on the first moving path information acquired based on the ultrasound signal received through the probe, and
generate and display the second moving path to be identifiable from the first moving path, based on the second moving path information,
wherein when the first and second moving paths overlap, the at least one processor is further configured to generate and display a ratio of a volume of an OOI corresponding to the first moving path and a volume of an OOI corresponding to the second moving path, in the overlapped region.

9. The ultrasound diagnostic apparatus of claim 8, wherein the at least one processor is further configured to set, as the first reference region, at least one of a point, a line, and a region in the ultrasound image.

10. The ultrasound diagnostic apparatus of claim 8, wherein the display is further configured to display the first and second moving paths in different colors.

11. The ultrasound diagnostic apparatus of claim 10, wherein when the first and second moving paths overlap, the display is further configured to display the overlapped region in a mixed color of a first color corresponding to the first moving path and a second color corresponding to the second moving path.

12. The ultrasound diagnostic apparatus of claim 8, wherein the at least one processor is further configured to trace a moving path of the OOI flowing out from the first reference region to acquire the first moving path information.

13. The ultrasound diagnostic apparatus of claim 8, wherein the at least one processor is further configured to trace a moving path of the OOI flowing into the first reference region from at least one other region in the ultrasound image to acquire the first moving path information.

14. The ultrasound diagnostic apparatus of claim 8, wherein the display is further configured to display a start region of the first moving path.

15. A non-transitory computer-readable storage medium storing a program for executing the method of claim 1.

* * * * *